(12) United States Patent
Taylor et al.

(10) Patent No.: US 8,841,080 B2
(45) Date of Patent: Sep. 23, 2014

(54) SYSTEM FOR DETERMINING UNPROCESSED AND PARTIALLY PROCESSED NEUROTOXIN TYPE A

(75) Inventors: Harold Victor Taylor, Frankfurt am Main (DE); Karl-Heinz Eisele, Frankfurt am Main (DE); Cornelia Brunn, Berlin (DE)

(73) Assignee: Merz Pharma GmbH & Co. KGaA, Frankfurt am Main (DE)

( * ) Notice: Subject to any disclaimer, the term of this patent is extended or adjusted under 35 U.S.C. 154(b) by 38 days.

(21) Appl. No.: 13/503,128

(22) PCT Filed: Oct. 18, 2010

(86) PCT No.: PCT/EP2010/065618
§ 371 (c)(1),
(2), (4) Date: Apr. 20, 2012

(87) PCT Pub. No.: WO2011/048044
PCT Pub. Date: Apr. 28, 2011

(65) Prior Publication Data
US 2012/0214182 A1    Aug. 23, 2012

Related U.S. Application Data

(60) Provisional application No. 61/279,453, filed on Oct. 21, 2009.

(51) Int. Cl.
| | |
|---|---|
| *G01N 33/53* | (2006.01) |
| *G01N 33/94* | (2006.01) |
| *G01N 33/573* | (2006.01) |
| *C07K 16/12* | (2006.01) |

(52) U.S. Cl.
CPC ...... *G01N 33/94* (2013.01); *G01N 2333/96419* (2013.01); *C07K 2317/34* (2013.01); *G01N 33/573* (2013.01); *C07K 16/1282* (2013.01)
USPC .......... 435/7.2; 435/7.32; 435/7.92; 435/7.94

(58) Field of Classification Search
CPC .... G01N 33/53; G01N 33/554; G01N 33/537
USPC ................................. 435/7.2, 7.32, 7.92, 7.94
See application file for complete search history.

(56) References Cited

U.S. PATENT DOCUMENTS

2006/0177881 A1    8/2006    Bavari et al.

FOREIGN PATENT DOCUMENTS

WO    2008/157374    12/2008

OTHER PUBLICATIONS

Jost, 2007. Drugs 67: 669
Beecher, 1997. J Protei Chem 16: 701-712.
Couesnon, 2006. Microbiology 152: 759.
Dressler, 2005. Mov Disord 20: 1617-16195.
Fischer, 2007. PNAS 104: 10447.
Krieglstein, 1990. Eur J Biochem 188: 39-45.
Krieglstein, 1991. Eur J Biochem 202: 41-51.
Krieglstein, 1994. J Protein Chem 13: 49-57.
Lindstrom, 2006. Clin Microbiol Rev 19(2): 298-314.
Pearce, 1994. Toxicol Appl Pharmacol 128: 69-77.
Silberstein, 2004. Pain Practice 4: 19-26.
Volland, 2008. J Immunnol Methods 330(1-2): 120-129.
IPRP for PCT/EP2010/065618 of Apr. 24, 2012.
International Search Report for PCT/EP2010/065618 of Nov. 16, 2010.
Kalb Suzanne R., et al, PLOS One, vol. 4, No. 4, Jan. 1, 2009.

*Primary Examiner* — Jennifer Graser
(74) *Attorney, Agent, or Firm* — Hueschen and Sage

(57) ABSTRACT

The present invention is concerned with tools for the quality control and safety during manufacture of neurotoxins. In particular, it relates to a method for the determination of the amount of partially processed and/or unprocessed *Botulinum* neurotoxin A polypeptide (BoNT/A) in a solution comprising processed and partially processed and/or unprocessed BoNT/A comprising the steps of contacting a sample of the solution with a capture antibody which specifically binds to the partially processed and unprocessed BoNT/A under conditions which allow for binding of the antibody to the partially processed and unprocessed BoNT/A, whereby a complex is formed, and determining the amount of the formed complex, whereby the amount of the complex is indicative for the amount of the partially processed and/or unprocessed BoNT/A in the solution. Moreover, the present invention contemplates a device and a kit for carrying out the method.

11 Claims, No Drawings

SYSTEM FOR DETERMINING UNPROCESSED AND PARTIALLY PROCESSED NEUROTOXIN TYPE A

The present invention is concerned with tools for the quality control and safety during manufacture of neurotoxins. In particular, it relates to a method for the determination of the amount of partially processed and/or unprocessed neurotoxin A polypeptide (BoNT/A) in a solution comprising processed and partially processed and/or unprocessed BoNT/A comprising the steps of contacting a sample of said solution with a capture antibody which specifically binds to the partially processed and unprocessed BoNT/A under conditions which allow for binding of said antibody to said partially processed and unprocessed BoNT/A, whereby a complex is formed, and determining the amount of the formed complex, whereby the amount of the complex is indicative for the amount of the partially processed and/or unprocessed BoNT/A in said solution. Moreover, the present invention contemplates a device and a kit for carrying out said method.

*Clostridium botulinum* and *Clostridium tetani* produce highly potent neurotoxins, i.e. *Botulinum* toxins (BoNTs) and tetanus toxin (TeNT), respectively. These Clostridial neurotoxins specifically bind to neuronal cells and disrupt neurotransmitter release. Each toxin is synthesized as an inactive unprocessed approximately 150 kDa single-chain protein. The posttranslational processing involves formation of disulfide bridges, and limited proteolysis (nicking) by the bacterial protease(s). Active neurotoxins consist of two chains, an N-terminal light chain of approx. 50 kDa and a C-terminal heavy chain of approx. 100 kDa, which are linked by a disulfide bond. The neurotoxins structurally and functionally consist of three domains, i.e. the catalytic light chain, the N-terminal half of the heavy chain encompassing the translocation domain and C-terminal half of the heavy chain containing the receptor binding site(s), see Krieglstein 1990, Eur J Biochem 188, 39; Krieglstein 1991, Eur J Biochem 202, 41; Krieglstein 1994, J Protein Chem 13, 49. The *Botulinum* neurotoxins are synthesized as molecular complexes comprising the 150 kDa neurotoxin protein and associated non-toxic complexing proteins. The complex sizes differ based on the Clostridial strain and the distinct neurotoxin serotypes ranging from 300 kDa, over 500 kDa, up to 900 kDa. The non-toxic complexing proteins in these complexes stabilize the neurotoxin and protect it against degradation, see Silberstein 2004, Pain Practice 4, S19-S26.

*Clostridium botulinum* secretes seven antigenically distinct serotypes of neurotoxins designated A to G. All serotypes together with the related TeNT secreted by *Clostridium tetani*, are $Zn^{2+}$-endoproteases that block synaptic exocytosis by cleaving SNARE proteins, see Couesnon, 2006, Microbiology, 152, 759. CNTs cause the flaccid muscular paralysis seen in botulism and tetanus, see Fischer 2007, PNAS 104, 10447.

Despite its toxic effects, the *Botulinum* toxin complex has been used as a therapeutic agent in a large number of diseases. *Botulinum* toxin serotype A (BoNT/A) was approved for human use in the United States in 1989 for the treatment of strabismus, blepharospasm, and other disorders and is, thus, of particular importance. It is commercially available as BoNT/A protein preparation, for example, under the tradename BOTOX (Allergan Inc) or under the tradename DYSPORT (Ipsen Ltd). An improved BoNT/A preparation which is free of complexing proteins is commercially available under the tradename XEOMIN (Merz Pharmaceuticals GmbH). For therapeutic applications, the preparation is injected directly into the muscle to be treated. At physiological pH, the toxin is released from the protein complex and the desired pharmacological effect takes place. The effect of *Botulinum* toxin is only temporary, which is the reason why repeated administration of *Botulinum* toxin may be required to maintain a therapeutic affect.

The Clostridial neurotoxins weaken muscle contraction and are effective therapy for strabismus, focal dystonia, including cervical dystonia, and benign essential blepharospasm. They have been further shown to relief hemifacial spasm, and focal spasticity, and moreover, to be effective in a wide range of other indications, such as gastrointestinal disorders, hyperhidrosis, and cosmetic wrinkle correction, see Jost 2007, Drugs 67, 669.

During the manufacturing process of Clostridial neurotoxins, the qualitative and quantitative determination as well as the quality control of the active neurotoxin polypeptide is of particular importance. Currently available neurotoxin preparations comprise different amounts of proteolytically unprocessed precursors and/or partially processed neurotoxin polypeptides in addition to the desired active (processed or mature) neurotoxins. The proteolytically unprocessed precursor or partially processed neurotoxin polypeptides differ from the mature (active, processed) neurotoxin polypeptides in only a few amino acids. Therefore, they can hardly be quantitatively distinguished based on their chemical and physical properties. On the other hand, the portion of proteolytically unprocessed precursor and/or partially processed neurotoxin polypeptides of the total protein content may still be significant in such preparations, i.e., relevant for the specific activity of the preparation.

Assays for determining the whole neurotoxin content in a preparation are well known in the art. These assays are based on Immuno-PCR or Sandwich ELISA (Lindstrom 2006, Clin Microbiol. Rev. 19(2): 298-314; Volland 2008, J Immunnol Methods 330(1-2): 120-129). However, as set forth above, the content of the undesired partially processed or unprocessed neurotoxins can not be determined by applying these techniques for assaying the whole neurotoxin content.

Accordingly, means and methods for determining the content of partially processed or unprocessed neurotoxin molecules and, in particular, BoNT/A molecules, in a preparation are not yet available but nevertheless highly desirable.

The present invention, thus, relates to a method for the determination of the amount of partially processed and/or unprocessed neurotoxin A polypeptide (BoNT/A) in a solution comprising processed and partially processed and/or unprocessed BoNT/A comprising the steps of:
  i) contacting a sample of said solution with a capture antibody which specifically binds to the partially processed and unprocessed BoNT/A under conditions which allow for binding of said antibody to said partially processed and unprocessed BoNT/A, whereby a complex is formed, and
  ii) determining the amount of the complex formed in step i), whereby the amount of the complex is indicative for the amount of the partially processed and/or unprocessed BoNT/A in said solution,
wherein the capture antibody is obtainable by a method comprising:
  a) contacting a polyclonal antiserum from an animal which has been immunized by a peptide immunogen comprising an amino acid sequence as shown in SEQ ID NO: 1 (TKSLDKGYNKA) to the following capture peptides SLD, LDK and YNK under conditions which allow for the formation of capture complexes comprising unspecific antibodies comprised by the polyclonal antiserum and the capture peptides;

b) removing the capture complexes from the polyclonal antiserum;

c) contacting the polyclonal antiserum to a peptide comprising or essentially consisting of SEQ ID NO: 1 under conditions which allow for the formation of a complex comprising the aforementioned peptide and an antibody specifically binds to unprocessed or partially processed neurotoxin polypeptide;

d) removing the complex formed in step c) from the antiserum; and e) releasing the antibody which specifically binds to unprocessed or partially processed neurotoxin polypeptide from the said complex.

The method of the present invention may be assisted by automation either entirely or at least in part. Such automation may include robotic devices as well as computer systems having implemented a suitable algorithm for the determination of the amount of the said partially processed and/or unprocessed BoNT/A in said solution. Moreover, the method of the invention may comprise additional steps carried out prior, after or in between steps i) and ii). Such additional steps, in an aspect, may include sample pre-treatment steps, washing or purification steps as well as data mining steps. In an aspect, said further steps include those referred to in the accompanying Examples below.

The term "partially processed and unprocessed neurotoxin A polypeptide (BoNT/A)" as used herein refers to neurotoxin serotype A polypeptides which are not yet mature, i.e. which have not been processed into the mature dichain polypeptide from the single-chain precursor or which have been merely partially processed. BoNT/A is one of the seven serotypes of Botulinum neurotoxins. It is produced as a single chain precursor molecule which is proteolytically processed after translation. The single chain molecule comprises an N-terminal light chain, a linker peptide, and a C-terminal heavy chain. During proteolytic processing of the single chain molecule, the linker peptide is excised so that a mature dichain molecule is generated comprising the heavy and the light chain but lacking the linker peptide. The linker peptide is, accordingly, flanked by two protease cleavage sites. Accordingly, during the process of proteolytic activation, partially processed molecules will occur. These partially processed molecules are merely cleaved at one of the flanking protease cleavage sites so that the linker peptide will still be linked to either the light or the heavy chain. Such molecules are termed partially processed BoNT/A polypeptides for the purpose of the present invention.

As a result of proper processing, "processed BoNT/A" is obtained. The said processed BoNT/A polypeptide exhibits the biological properties characteristic for a neurotoxin, namely, (a) receptor binding, (b) internalization, (c) translocation of the light chain across the endosomal membrane into the cytosol, and/or (d) endoproteolytic cleavage of proteins involved in synaptic vesicle membrane fusion. Therefore, the processed BoNT/A polypeptide is sometimes referred to herein as active or mature neurotoxin polypeptide. The biological activity, in an aspect, results from all of the aforementioned biological properties. In vivo assays for assessing biological activity include the mouse LD50 assay and the ex vivo mouse hemidiaphragm assay as described by Pearce 1994, Toxicol Appl Pharmacol 128: 69-77 and Dressler 2005, Mov Disord 20:1617-1619. The biological activity is commonly expressed in Mouse Units (MU). As used herein, 1 MU is the amount of neurotoxic component, which kills 50% of a specified mouse population after intraperitoneal injection, i.e. the mouse i.p. LD50.

In an aspect, BoNT/A is obtained from the Hall strain of Clostridium botulinum and, in a further aspect, has a structure (i.e. an amino acid sequence) as disclosed in Beecher 1997, J Protein Chem 16: 701-712 or Krieglstein 1994, J Protein Chem 13: 49-57. Moreover, amino acid for and nucleic acid sequences encoding BoNT/A are to be found under GenBank Accession numbers ABD65472.1 or GI:89258592 or shown in SEQ ID NOs: 2 or 3, respectively. The protease cleavage sites flanking the linker peptide are, in an aspect, between amino acids K438/T439 and K448/A449. Thus, the linker peptide consists essentially of amino acid T439 to amino acid K448.

However, also encompassed by the method of the present invention are variants of the aforementioned BoNT/A. Said variants, in an aspect, are a neurotoxin polypeptides having an amino acid sequence comprising at least one amino acid addition, substitution and/or deletion compared to the amino acid sequence of the BoNT/A as shown SEQ ID NO: 2 or the amino acid sequence encoded by SEQ ID NO: 3. In yet another aspect, the variant neurotoxins comprise an amino acid sequence being at least 40% identical to the amino acid sequence of the BoNT/A as shown SEQ ID NO: 2 or the amino acid sequence encoded by SEQ ID NO: 3. The aforementioned amino acid sequences shows the amino acid sequence of unprocessed BoNT/A polypeptide. The sequences of the corresponding partially processed or processed neurotoxin polypeptides can be deduced from the said sequences by the information on cleavage sites and the linker peptide given elsewhere herein. In another aspect of the invention, the variant BoNT/A polypeptide has an amino acid sequence being at least 40%, at least 50%, at least 60%, at least 70%, at least 75%, at least 80%, at least 85%, at least 90%, at least 95%, at least 98% or at least 99% sequence identical to the amino acid sequence as shown in SEQ ID NO: 2 or the amino acid sequence encoded by the nucleotide sequence of SEQ ID No: 3. Identical as used in the present invention refers to sequence identity of amino acid sequences wherein the sequences are aligned so that the highest order match is obtained. This can be achieved by using published techniques or methods codified in computer programs such as, for example, BLASTP, BLASTN, FASTA, Altschul 1990, J Mol Biol 215, 403. The percent identity values are, in one aspect, calculated over the entire amino acid sequence. A series of programs based on a variety of algorithms is available to the skilled worker for comparing different sequences. In this context, the algorithms of Needleman and Wunsch or Smith and Waterman give particularly reliable results. To carry out the sequence alignments, the program PileUp (1987, J Mol Evolution 25, 351; Higgins 1989 CABIOS 5, 151) or the programs Gap and BestFit (Needleman 1970, J Mol Biol 48; 443; Smith 1981, Adv Appl Math 2, 482), which are part of the GCG software packet (Genetics Computer Group 1991, 575 Science Drive, Madison, Wis., USA 53711), are to be used. The sequence identity values recited above in percent (%) are to be determined, in one aspect of the invention, using the program GAP over the entire sequence region with the following settings: Gap Weight: 50, Length Weight: 3, Average Match: 10.000 and Average Mismatch: 0.000, which, unless otherwise specified, shall always be used as standard settings for sequence alignments.

It will be understood that the aforementioned variants shall, in an aspect of the invention, retain, at least one, and, in an aspect all, of the biological properties of BoNT/A. It is envisaged in a further aspect that the partially processed and unprocessed variant BoNT/A polypeptides can be specifically bound by the antibody to be applied in the method of the invention. In an aspect, this can be achieved by the presence of a peptide sequence comprising SEQ ID NO: 1 in the linker peptide.

In a further aspect, the variants of BoNT/A can be neurotoxins having improved or altered biological properties, e.g., they may comprise cleavage sites which are improved for enzyme recognition or may be improved for receptor binding or any other property specified above.

In general, it is conceivable to modify the method of the present invention since the underlying concept relies on the presence of at least one cleavage site between light and heavy chain of the neurotoxin polypeptide while the nature of the cleavage sites and the particular amino acid sequence between them does not matter as long as the antibody to be applied in the method is capable of specifically recognizing the partially processed or unprocessed neurotoxin polypeptides. Accordingly, it is another aspect to apply variant neurotoxins wherein the protease recognition sites and/or the linker peptide between heavy- and light chain have been replaced. It will be understood that the antibody to be applied in this aspect shall still specifically bind to the linker peptide or an epitope thereof.

In yet another aspect, the linker peptide of BoNT/A comprising SEQ ID NO:1 can be introduced, e.g., by nucleic acid recombination techniques, into the linker of other neurotoxin serotypes and the amount of unprocessed and partially processed polypeptides of said other neurotoxin serotypes can be determined in a sample by applying the method of the present invention.

The term "amount" as used in the method of the present invention encompasses the absolute amount of a polypeptide, the relative amount or the concentration of the said polypeptide as well as any value or parameter which correlates thereto or can be derived therefrom.

The term "solution" as used herein refers to any solvent system containing mature BoNT/A polypeptides and the partially processed and/or unprocessed BoNT/A polypeptide precursors. The solvent system furthermore comprises a solvent. The solvents encompassed, in various aspects of the invention, are water, aqueous buffer systems, organic solvents, and ionic liquids. In one aspect of the invention, it is an aqueous solvent system. Moreover, the solvent system, in addition to the mature BoNT/A polypeptide and the partially processed or unprocessed precursor polypeptide and the solvent may comprise further molecules as well, including further bacterial polypeptides. In an aspect, the solution to be applied in the method of the present invention will be a bacterial cell culture or a partially purified or purified preparation obtained from such a bacterial cell culture.

The term "sample" as used herein refers to a portion of the said solution which will be investigated by the method of the invention. It will be understood that the sample shall also comprise the BoNT/A and the partially processed and/or unprocessed BoNT/A precursors. In an aspect of the method of the invention, said sample has a predefined volume and/or a predefined total protein content. In a further aspect, the sample may comprise exogenously supplied molecular standards.

Contacting a sample of the solution to the capture antibody as used in accordance with the method of the invention refers to bringing the aforementioned unprocessed and/or partially processed BoNT/A polypeptides comprised by the sample and the capture antibody into physical proximity as to allow physical and/or chemical interaction. Suitable conditions which allow for specific interaction are, in principle, well known to the skilled worker. Said conditions will depend on the antibodies and the solution to be applied in the method of the present invention and can be adapted by the skilled artisan without further ado. Moreover, a time being sufficient to allow interaction can also be determined by the skilled worker without further ado. It will be understood that the said time will depend on exogenous factors under which the method is carried out such as temperature, solvent composition, pH value etc. Moreover, it is to be understood that between the individual steps of contacting recited in the method of the present invention, washing steps may be performed in order to obtain suitable conditions for contacting. For example, after formation of a complex in step i), the remaining solution shall be removed prior to applying the detection agent for the said complex.

In an aspect of the method of the present invention, a detergent is present during step i). Accordingly, it is envisaged that prior or during step i) a detergent shall be added to the sample. Suitable detergents include ionic and non-ionic detergents. In an aspect, the detergent is a non-ionic detergent, and, in yet a further aspect, Tween 20.

In an aspect of the method of the present invention, said detergent is present at a concentration in the range of 0.01% (v/v) to 10% (v/v). In a further aspect, said concentration is in the range of 0.2% (v/v) to 0.8% (v/v) or in the range of 0.3% (v/v) to 0.6% (v/v), and, in still another aspect, the concentration is 0.5% (v/v).

In another aspect of the method of the present invention, said conditions in step i) comprise the presence of a phosphate-buffered or tris-buffered saline solution. In an aspect, said saline solution comprises NaCl at a concentration in the range of 150 to 350 mM. In yet another aspect, said concentration is in the range of 200 to 300 mM, and, in still another aspect, the concentration is 250 mM.

The term "determining the amount" as used herein relates to measuring the absolute amount, relative amount or concentration in a quantitative or semi-quantitative manner. Measuring will be done based on the chemical, physical or biological properties of the complex formed in step i). The said amount of the said complex may be determined directly or indirectly. In an aspect, a detection agent will be applied which interacts with the formed complexes. The detection agent will comprise or generate a detectable label which correlates to the amount of detected complexes and, thus, allows for determining the amount thereof. In an aspect, the said detection agent binds to the capture antibody or the unprocessed or partially processed BoNT/A present in the complexes. Accordingly, in a further aspect, the detection agent shall be an antibody, binding peptide (e.g. a BoNT/A receptor or part thereof), aptamer or small molecule compound which binds to either the capture antibody or the partially processed or unprocessed BoNT/A or both when present in the complex formed in step i).

A detection agent, in an aspect, comprises a detectable label. In an aspect, a detectable label has fluorescent or chemoluminescent properties and, thus, allows for a direct detection of the detection agent. Typical fluorescent labels include fluorescent proteins (such as GFP and its derivatives), Cy3, Cy5, Texas Red, Fluorescein, and the Alexa dyes (e.g. Alexa 568). In yet another aspect, the label may be a radioactive label. Typical radioactive labels include $^{35}S$, $^{125}I$, $^{32}P$, $^{33}P$ and the like. In still another aspect, the detection agent may comprise an enzymatic activity which is capable of generating a detectable signal, e.g., by conversion of a substrate. Typically, such an enzyme may be a peroxidase (e.g., horseradish peroxidase), firefly luciferase or alkaline phosphatase. Labels of the aforementioned type can be coupled directly (covalently or non-covalently) to the detection agent. Besides the said direct labeling, the detection agent may be indirectly labeled in another aspect of the method of the invention. Said indirect labeling involves binding (covalently or non-covalently) of an agent which specifically binds to the detection agent and which carries a detectable label. Such an agent may be, e.g., a secondary (higher order) antibody which specifically binds to the detection agent. The secondary antibody in such a case will be coupled to a detectable label. It will be understood that further higher order antibodies can be used in addition for detection of the detection complex. The higher order antibodies are often used to increase the signal. Suitable higher order antibodies may also include commercially available labeling systems such as the streptavidin-biotin system (Vector Laboratories, Inc.), the Dako LSAB™2 and LSAB™+ system (labeled streptavidin-biotin), or Dako PAP system (Peroxidase Anti-Peroxidase).

It will be understood that the amount of detectable label comprised or generated by the detection agent correlates directly to the amount of complexes. The amount of complexes again correlates to the amount of molecular species to be determined, i.e. to the unprocessed and/or partially processed neurotoxin molecules present in the sample. It will be understood, furthermore, that the sample is a representative portion of the solution. Accordingly, the amount of unprocessed and/or partially processed BoNT/A polypeptides determined for the sample is indicative for the amount present in the solution.

The determination of the amount of unprocessed and partially processed neurotoxin polypeptides, in an aspect, also requires calibration of the method by applying standard solutions with predefined amounts of said polypeptides. How to carry out such a calibration is well known to those skilled in the art. In an aspect, several determinations are carried out by applying the method of the present invention for samples of two or more the aforementioned standard solutions differing in the predefined amount of unprocessed and/or partially processed neurotoxins.

Accordingly, in an aspect of the method of the present invention, said step ii) comprises comparing the determined amount of the complex with a reference. In an aspect, the reference is a calibration curve derived from two or more standard solutions as described above. As a result of the comparison, the determined complex amounts can be allocated to predefined amounts of unprocessed and/or partially processed BoNT/A polypeptides.

Unprocessed BoNT/A polypeptides can be obtained from a *Clostridium botulinum* mutant expressing BoNT/A polypeptide precursors being mutated in the cleavage sites for the protease. Such mutants can be generated by standard molecular biology techniques well known in the art. Moreover, unprocessed BoNT/A can be obtained by expressing the said BoNT/A recombinantly in *E. coli* or other bacteria lacking a protease capable of activating the BoNT/A by proteolytic cleavage. In another aspect, *Clostridium botulinum* bacterial cells or other expression systems can be mutated in order to screen for mutants having significantly reduced or even no protease activity and, thus, only produce unprocessed neurotoxins.

The method of the present invention requires a capture antibody which specifically binds to the partially processed and unprocessed BoNT/A polypeptides. Such an antibody is, in an aspect, obtainable by a method referred to above comprising steps a) to e) referred to above. The terms used in this context are further explained in the following.

The term "antibody" as used herein encompasses a monoclonal antibody, a polyclonal antibody, a single chain antibody, a human, humanized, primatized, or chimerized antibody, a bispecific antibody, a synthetic antibody, chemically or enzymatically modified derivatives, a fragment of any of said antibodies or aptamers consisting of naturally occurring and/or chemically modified nucleic acids. Fragments of said antibodies include $F(ab')_2$, $F(ab)$, Fv or scFv fragments or chemically or enzymatically modified derivatives of any of these fragments. The antibody of the present invention shall specifically bind to the epitope consisting of the aforementioned peptide if the said peptide is comprised by the partially processed or the unprocessed neurotoxin polypeptide.

The term "specifically binds" means that the antibody of the present invention does not cross react to a significant extent with other epitopes either on said partially processed, or on said unprocessed neurotoxin polypeptides, or on other polypeptides in general. In an aspect of the invention, the antibody of the present invention does not cross react with said active, completely processed neurotoxin polypeptide. Epitope specificity is an important characteristic of the antibody of the present invention. Specificity of the antibody with respect to the partially processed or unprocessed neurotoxin versus the processed neurotoxin shall be, in an aspect, at least 95%, at least 96%, at least 97%, at least 98%, at least 99%. Specific binding can be tested by various well known techniques including, e.g., competition studies or Western blot analysis of SDS PAGE. Another important characteristic is the sensitivity of the antibody. Sensitivity shall be, in one aspect of the invention, such that at least 70%, at least 80%, at least 90%, at least 95% of the processed neurotoxin comprised by a sample is bound. Sensitivity can be tested by well known techniques. Those skilled in the art will be able to determine operative and optimal assay conditions for each determination by employing routine experimentation. Conventional techniques for binding studies include radioimmunoassay, ELISA, equilibrium dialysis, isothermal microcalorimetry, BIACORE® assays (surface plasmon reasonance, SPR) or other surface adsorption methods. The binding properties such as sensitivity of an antibody of the present invention may, in principle, be determined by binding studies using an immobilized antigen (the ligand) presented on a sensor surface. The antibody to be tested (the analyte) will be provided in the mobile phase, i.e. in a solution. In some cases, the antigen is attached indirectly to the surface through binding to another immobilized molecule which is referred as the capturing molecule. When the antibody is injected in a discrete pulse across the surface with the immobilized antigens, essentially three phases can be subdivided: (i) Association of antibody with the antigen during sample injection; (ii) Equilibrium or steady state during sample injection, where the rate of antibody binding is balanced by dissociation from the antibody-antigen complex; (iii) Dissociation of antibody from the surface during buffer flow. It will be understood that such an assay can alternatively performed with immobilized antibodies to be investigated and an antigen containing solution as the mobile phase. The association and dissociation phases provide information on the kinetics of analyte-ligand interaction ($k_a$ and $k_d$, the rates of complex formation and dissociation, $k_d/k_a=K_D$). The equilibrium phase provides information on the affinity of the analyte-ligand interaction ($K_D$). In an aspect of the invention, the antibody of the present invention has a KD of less than 0.5 µM, in an aspect, less than 0.05 µM and, in another aspect, less than 0.02 µM.

The antibody to be applied in the method of the invention, in an aspect, allows for the detection of partially processed and/or unprocessed neurotoxin polypeptide with a high sensitivity and specificity, in an aspect with a limit of detection of <1000 pg/mL, <300 pg/mL, <100 pg/mL, in an aspect 50 to 80 pg/mL, and in yet another aspect 69 pg/mL. In a further aspect, the limit of detection may even be <30 pg/mL, <10 pg/mL, <3 pg/mL, and, in an aspect about or <1 pg/mL.

The antibody as referred to in the present invention can be manufactured by using methods which are described, e.g., in Harlow and Lane "Antibodies, A Laboratory Manual", CSH Press, Cold Spring Harbor, 1988. Monoclonal antibodies can be prepared by the techniques originally described in Köhler 1975, Nature 256, 495, and Galfré 1981, Meth Enzymol 73, 3. Said techniques comprise the fusion of mouse myeloma cells to spleen cells derived from immunized mammals. Antibodies can be further improved by techniques well known in the art. For example, surface plasmon resonance as employed in the BIACORE® system can be used to increase the efficiency of phage antibodies which bind to the aforementioned epitope within proteolytically unprocessed neurotoxin polypeptide, see Schier 1996, Human Antibodies Hybridomas 7, 97; Malmborg 1995, J. Immunol Methods 183, 7.

The term "peptide immunogen" as used above refers to an oligopeptide having an amino acid sequence as shown in SEQ ID NO: 1 which is provided in a manner as to allow eliciting an immune response in a non-human animal.

In an aspect, said peptide having SEQ ID NO: 1 is coupled to a carrier protein via any linker or linking procedure known in the art.

In another aspect, said immunogen further comprises keyhole limpet hemocyanin (KLH). In a further aspect, said KLH is linked to the peptide having SEQ ID NO: 1 via the linker N-[gamma-maleimidobutyryloxy] succinimide ester (GMBS). In yet a further aspect, said KLH is linked via a cysteine and, in an aspect a C-terminal cysteine, to the peptide having SEQ ID NO: 1 via the linker GMBS. How to link KLH to a peptide by a linker molecule such as GMBS is well known in the art or described in the accompanying Examples below.

In another aspect, ovalbumine can be used as an immunogen. The said ovalbumine will be cross-linked via the linker sulfosuccinimidyl-4-(N-maleimidomethyl)cyclohexane-1-carboxylate (sulfo-SMCC) to a cysteine residue, in an aspect, to a C terminal cysteine residue. In this aspect, it is envisaged to use a pentapeptide consisting of amino acids X to Y of SQ ID NO: 1 to which the aforementioned cysteine is added C-terminally.

In another aspect the non-human animal is a mammal, in an aspect a rat, mouse, rabbit, sheep or goat. Prior to carrying out the method of the invention, a non-human animal which shall be the source of the polyclonal antiserum will be immunized using the aforementioned peptide immunogen. How to immunize a non-human animal is well known in the art and described in the accompanying Examples, below. As a result of the said immunization, the non-human animal will produce polyclonal antibodies against the peptide immunogen.

A polyclonal antiserum can be obtained from the non-human animal by various techniques. In an aspect it is obtained from blood, serum or plasma by standard techniques well known in the art and described in the accompanying Examples, below. The term "polyclonal antiserum", thus, includes purified and partially purified sera from the said animal. Such a polyclonal antiserum is the starting material for the aforementioned method. In addition to the desired one or more antibodies which specifically bind to unprocessed and partially processed BoNT/A polypeptide, the polyclonal antiserum may comprise additional antibodies which do not specifically bind to unprocessed and partially processed BoNT/A polypeptide.

These undesired, cross-reactive antibodies are separated form the desired specific antibodies by contacting the said polyclonal antiserum with the capture peptides SLD, LDK, and YNK under conditions which allow for the formation of capture complexes comprising unspecific antibodies comprised by the polyclonal antiserum and the capture peptides and removing the capture complexes from the polyclonal antiserum in order to obtain a partially purified polyclonal antiserum. The aforementioned capture peptides can be applied in the method, in an aspect, in the form of their derivatives disclosed in the accompanying Examples, below.

The said partially purified polyclonal antiserum is subsequently contacted with a peptide also having an amino acid sequence as shown in SEQ ID NO: 1. In an aspect, said peptide is immobilized on a carrier as described in detail elsewhere herein. As a result of the said contacting, a complex of the peptide and the specific antibodies is formed which can subsequently be removed from the remaining polyclonal serum. The specific antibodies than can be released from the removed complex. Suitable techniques for releasing antibodies from such a complex are described elsewhere herein.

In an aspect, steps a) to e) of the method for obtaining the antibody are carried out by means of affinity chromatography. Affinity chromatography as used in the present invention refers to a technique for separating molecules in a mobile phase based on their different affinities for a stationary phase used in the chromatography. In an aspect, the said technique refers to selective adsorption and subsequent recovery of a compound from an immobilized ligand. In another aspect, the said technique is designed for highly specific and efficient purification of proteins and related compounds using appropriate selective ligands on beaded and porous matrices for binding target compounds, which can then be recovered under mild conditions. The said technique is based on a highly specific interaction such as that between antigen and antibody, enzyme and substrate, or receptor and ligand. In another aspect said affinity chromatography is perform as column chromatography. Affinity chromatography as characterized in detail above is in one aspect, immunoabsorber chromatography and, hydrophobic interaction chromatography (HIC), reverse phase chromatography, and in another aspect, immunoaffinity chromatography applying the binding agent which is in even a further aspect, the antibody of the present invention. A stationary phase as referred to herein in an aspect consists of the aforementioned agent as a solid matrix. Said agent is in one aspect, bound to a polypeptide carrier coupled to a solid matrix, and in another aspect, bound to Protein A coupled to a solid matrix.

For carrying out the method of the invention, the capture antibody can be coupled covalently or non-covalently to a solid support. Materials for such solid supports are well known in the art and include, inter alia, commercially available polysaccharide matrices selected from the group consisting of: SEPHAROSE®, SEPHADEX®; agarose, SEPHACEL®, micro-cellulose, and alginate-beads, polypeptide matrices, polystyrene beads, latex beads, magnetic beads, colloid metal particles, glass, plastic and/or silicon chips and surfaces, nitrocellulose strips, membranes, sheets, duracytes, wells and walls of reaction trays, plastic tubes. In an aspect of the invention, said solid support is made of gamma-irradiated polystyrene. Dependent on the intended applications, the said solid support may be comprised by or in form of separate vials. Alternatively, the solid support may be comprised by or be in form of multi-well plates. Dependent on the solid support, it might be necessary to carry out blocking steps prior to the application of the solid support in the method off the present invention in order to block free binding sites of the solid support for peptides and proteins.

Advantageously, the method of the present invention allows for the specific determination of BoNT/A precursor molecules, i.e. unprocessed, single chain BoNT/A and/or partially processed BoNT/A. These precursor molecules are usually undesired contaminants in BoNT/A preparations to be applied for therapeutic or cosmetic purposes. Accordingly, their content shall be reduced to a minimum amount. The method of the present invention allows establishing an efficient quality control and product safety management for the manufacture of BoNT/A preparations. Moreover, the efficacy of purification and/or processing steps can be monitored when manufacturing BoNT/A preparations. In the studies underlying the invention, a polyclonal serum was raised against unprocessed *Botulinum* neurotoxin type A (BoNT/A), using the linker peptide coupled to KLH as immunogen (anti-linker peptide scBoNT/A-serum) in goats. Even after affinity purification, the serum showed cross-reactivity towards processed BoNT/A in a Western blot analysis of SDS PAGE. It was demonstrated that the cross-reactivity depended on the recognition of tripeptides (SLD, LDK and YNK), which occurred in the linker peptide, as well as, in the light and heavy chains of processed BoNT/A. A second batch of the goat immunoserum was purified via two-step affinity chromatography, removing the cross-reactive tripeptide-antibodies. The second anti-linker peptide scBoNT/A-serum displayed no cross-reactivity against processed BoNT/A in a western blot.

In an aspect, the method of the present invention comprising the aforementioned general steps comprises further the following specific steps:

1) Immobilizing on a solid support (e.g., a multi well plate) the capture antibodies obtained by the above mentioned method;
2) Removing non-immobilized capture antibodies by washing;
3) Blocking of free peptide/protein binding sites on the solid support by applying a suitable blocking buffer (see Examples below);
4) Removing blocking buffer by washing;
5) Applying samples of solutions to be analyzed or of standard solutions used for calibration under conditions which allow formation of the capture complex;
6) Removing the unbound sample material by washing;
7) Applying a detection agent (e.g., a first and, optionally, higher order detection antibody which is directly or indirectly coupled to an enzyme such as peroxidase) under conditions which allow for formation of a detection complex;
8) Removing unbound detection agent by washing;
9) Determining the detection signal elicited by the detection agent (e.g., by applying a chromogenic substrate to the detection complex and measuring the substrate conversion by determining the optical density).

It will be understood, however, that the method of the invention can also be implemented by any other specific steps derivable from the above.

The present invention also contemplates a device for the determination of the amount of partially processed and/or unprocessed neurotoxin A polypeptide (BoNT/A) in a solution comprising processed and partially processed and/or unprocessed BoNT/A polypeptides comprising:

i) an analysis unit comprising a capture antibody as specified above wherein the analysis unit allows for contacting a sample of said solution with the said capture antibody, and
ii) an evaluation unit comprising a reader system for determining the amount of the complex formed in the analysis unit and a data processing system allowing for the calculation of the amount of the partially processed and/or unprocessed BoNT/A polypeptides in said solution based on the determined amount of the complex.

The term "device" as used herein relates to a system comprising at least the aforementioned arrangement of an analysis unit and an evaluation unit operatively linked to each other as to allow the determination. In an aspect, the arrangement can be a solid support with immobilized capture antibodies as referred to above which may be present on a solid support as specified above, e.g., in form of a vial, in order to allow contacting of a sample of the solution and the capture antibody. Moreover, the device may comprise, in an aspect, a reader system for the determination of the amount of the detection complexes. Dependent on the kind of detection agent to be used, such a system will comprise a detector for the generated signals. Moreover, the unit can also comprise, in an aspect, a computer-based algorithm for processing of the data obtained from the reader system. Said algorithm shall allow for calculation of the amount of the desired polypeptides. In an aspect, this is achieved by comparing the measured signals to the calibration standards in order to determine the amounts of the polypeptides present in a solution or a sample thereof.

Moreover, the present invention encompasses a kit for the determination of the amount of partially processed and/or unprocessed neurotoxin A polypeptide (BoNT/A) in a solution comprising processed and partially processed and/or unprocessed BoNT/A polypeptides comprising a capture antibody as specified above.

The term "kit" as used herein refers to a collection of the aforementioned capture antibody and, in an aspect, a detection agent and/or one or more calibration standards as set forth elsewhere herein. The said components of the kit may or may not be packaged together. The components of the kit may be comprised by separate vials (i.e. as a kit of separate parts) or provided in a single vial. Moreover, it is to be understood that the kit of the present invention is to be used for practicing the methods referred to herein above. In one aspect, it is envisaged that all components are provided in a ready-to-use manner for practicing the methods referred to above. In a further aspect, the kit contains instructions for carrying out the said methods. The instructions can be provided by a user manual in paper- or electronic form. For example, the manual may comprise instructions for interpreting the results obtained when carrying out the aforementioned methods using the kit of the present invention.

In an aspect of the kit of the invention, said kit further comprises at least one detection agent for determining the amount of a complex comprising the capture antibody and unprocessed and/or partially processed BoNT/A polypeptides.

All references cited in this specification are herewith incorporated by reference with respect to their entire disclosure content and the disclosure content specifically mentioned in this specification.

EXAMPLES

Example 1

Generation of Immunogen and Antibodies

Generation of Immunogens

1. Linkerpeptide-Immunogen I: The peptide with the sequence NH$_2$-TKSLDKGYNK-Cys-COOH (SEQ ID NO: 8) was generated by an external provider and then coupled by the linker GMBS to the carrier-protein KLH.

2. Linkerpeptide-Immunogen II: a) Activation of ovalbumin; 2.18 mg sulfo-SMCC (sulfosuccinimidyl-4(N-maleimidomethyl)cyclohexane-1-carboxylate) were solved in 50 μL DMSO. Subsequently, 2.5 mL ovalbumin solution containing 7.5 mg/mL ovalbumin (buffer: 5 mM sodium phosphate; 0.9% NaCl) were added and the solution was incubated for 1 h at room temperature with rotation. A buffer change was performed using PD10 columns, activated ovalbumin was eluted in 3.5 mL buffer containing 10 mM sodium phosphate; 0.9% NaCl. b) Coupling of the peptide to ovalbumin; 8 mg of the peptide Ac-DKGYN-Cys-COOH (SEQ ID NO: 9) were solved in 250 μL H$_2$O and 2.5 μL 500 mM TCEP.HCl (tris[2-carboxyethyl]phosphine hydrochloride) and subsequently neutralized with 1 mM NaOH. Finally, activated ovalbumin was added and the reaction mixture was incubated at room temperature for 4.4 h with rotation. By adding a 10 mM cysteine solution remaining reactive groups were blocked by incubation for 1 h with rotation. A dialysis was performed using 10 mM sodium phosphate; 0.9% NaCl.

Immunization

Antisera were obtained by immunization.

1.) Anti-linkerpeptide scBoNT/A-serum I: As immunogen the Linkerpeptide-Immunogen I was used which was coupled by the linker GMBS to the carrier-protein KLH. Two goats were immunized by subcutaneous injection of Linkerpeptide-Immunogen I, each initially with 300 μg Linkerpeptide-Immunogen I dissolved in Freud's adjuvant and finally immunized for four times in a 2 week rhythm with 100 μg Linkerpeptide-Immunogen I in incomplete Freud's adjuvant. Antisera were collected after 49, 63, 77 and 84 days. Affinity chromatography was performed using the serum collected from the final bleeding on day 84.

2.) Anti-linkerpeptide scBoNT/A-serum II: As immunogen the Linkerpeptide-Immunogen II was used which was coupled to the carrier-protein ovalbumin by the linker SMCC. Two rabbits were immunized by intradermal injection of Linkerpeptide-Immunogen II, each initially with 300 μg Linkerpeptide-Immunogen II in Freud's adjuvant and finally immunized for five times in a 2 week rhythm with 150 μg Linkerpeptide-Immunogen II in MONTANIDE® ISA 206. Affinity chromatography was performed using the serum collected from the bleeding on day 60 or 110, respectively.

Two Step Affinity Chromatography of the Sera

1. Generation of the matrix: Two different ultra link iodoacetyl matrices containing different peptides were generated for the two-step affinity chromatography.

On the one hand, the cross reactive peptides SLD, LDK and YNK were presented in form of the following peptides Ac-ELDKYN-Cys-COOH (SEQ ID NO: 4), NH$_2$-NISLDL-Cys-COOH (SEQ ID NO: 5) and NH$_2$-YYNKF-Cys-COOH (SEQ ID NO: 6) and were coupled to the matrix using the general description given below. On the other hand the linker peptide (SEQ ID NO: 1) was coupled to the matrix using the general description given below in the form of the following derivative: Ac-TKSLDKGYNKA-Cys-COOH (SEQ ID NO:7).

General Description:

Coupling Buffer: 50 mM Tris, 5 mM EDTA-Na, pH 8.5. Prepare a volume of buffer equal to 20 times the volume of UltraLink® Iodoacyl Gel to be used.

L-Cysteine HCl; Wash solution: 1 mM sodium chloride (NaCl).

Empty gravity-flow or spin column that may be capped both top and bottom.

Prepare the Peptide or Protein Sample

Dissolve the peptide with Coupling Buffer.

Couple to UltraLink® Iodoacyl Gel:
1. With the bottom cap in place on a gravity-flow column, add the desired quantity of the UltraLink® Iodoacyl Gel slurry, allow the gel to settle for 15 minutes.
2. Drain the liquid from the packed column and wash/equilibrate the UltraLink® Iodoacyl Gel with 5 gel-bed volumes of Coupling Buffer by adding buffer to the top of the gel bed allowing to drain through the column. Do not allow the gel bed to run dry.
3. Replace bottom cap and add the prepared sulfhydryl-containing sample. Approximately 1 mL of sample solution can be applied per mL of UltraLink® Iodoacyl Gel.
4. Replace the top cap and mix column at RT for 15 minutes.
5. Stand the column upright and incubate at RT for 30 minutes without mixing.
6. Sequentially remove top and bottom column caps and allow the solution to drain.
7. Wash column with three gel-bed volumes of Coupling Buffer.

Block Nonspecific Binding Sites on Gel.
1. Replace the bottom cap on column.
2. Prepare a solution of 50 mM L-Cysteine HCl in Coupling Buffer and add 1 mL of this solution to the column for each milliliter of gel.
3. Replace the top cap and mix for 15 minutes at RT, then incubate the reaction without mixing for an additional 30 minutes at RT.

2. Two step affinity chromatography: Sera to be purified are first separated from blood. The crude serum is applied to the first column containing the cross reactive tripeptides. The cross reactive antibodies bind to the tripeptides and are thus separated from the crude serum. The flow-through of this first column is applied to the second column containing the bound linkerpeptide. The linkerpeptide specific antibodies bind to the linkerpeptide and are thus separated from the crude serum which is found in the second flow-through of the second column. Low affinity anti-linkerpeptide scBoNT/A antibodies are removed from the column by a high stringency wash with PBS buffer (0.5 M NaCl). Subsequently, the bound high affinity anti linkerpeptide scBoNT/A antibodies are eluted and concentrated. This concentrate corresponds to the used anti linkerpeptide scBoNT/A serum.

Example 2

Test and Verification of Antibody Specificity

Reagents ELISA:
Coating buffer: 0.005 M-1M Tris; 0.9% NaCl, preferable 0.01 M-0.2 M Tris; 0.9% NaCl, pH=8.5.
Capture antibody: anti-linkerpeptide scBoNT/A serum.
Blocking and antibody diluent buffer: 0.5%-5% BSA in 0.01 M sodium phosphate; 0.9% NaCl, pH=7.4.
Sample buffer: 0.5%-5% BSA in 0.005 M-1 M sodium phosphate; 0.1-0.5 M NaCl; 0.01%-1% Tween 20, preferably 1%-3% BSA in 0.005-0.1 M sodium phosphate; 0.15 M-0.4 M NaCl; 0.05%-0.5% Tween 20, pH=7.4.
Wash buffer: 0.01 M sodium phosphate; 0.9% NaCl; 0.05% Tween 20, pH=7.4.
Detection antibody: monoclonal antibody against BoNT/A.
Secondary antibody: A polyclonal anti mouse IgG (H&L) antibody conjugated to peroxidase.
Substrate: TMB, commercially available.

2. Reagents Western Blot:
Denaturating sample buffer, commercially available.
SDS gel, commercially available.

MES running buffer (SDS PAGE): commercially available.
PVDF membrane: commercially available.
Transfer buffer (Western Blot): commercially available.
Sample: *Botulinum* Neurotoxin A with Dichain-BoNT/A and scBoNT/A.
Primary antibody: anti linkerpeptide scBoNT/A serum.
Secondary antibody: polyclonal donkey anti goat antibody IgG (H&L) conjugated to alkaline phosphatase.
Blocking and antibody diluent buffer: 0.5%-5% BSA in 0.01 M-0.1 M Tris; 0.9% NaCl; 0.05%-5% Tween 20, pH=7.4.
Washing buffer: 0.01 M-0.1 M Tris; 0.9% NaCl; 0.05%-5% Tween 20, pH=7.4.
Tris buffer: 0.025 M Tris, pH=8.0.
Substrate: BCIP/NBT, commercially available.

a) Specificity of the antiserum with regard to BoNT/B and BoNT/E: To determine the specificity of the antisera with regard to BoNT/B and BoNT/E, the recovery rate of substances were analyzed in ELISA. Microtiter plates are incubated with 100 µL/well of coating buffer containing 0.5 µg anti linkerpeptide scBoNT/A-serum/mL for 16 h at room temperature and subsequently washed three times with washing buffer. 200 µL/well blocking solution is added to the microtiter plates and incubated for 1 h at room temperature. The antigen scBoNT/A (dilution series in sample buffer; pg/mL concentration) is used as a calibration standard, microtiter plates are incubated with 100 µL/well calibration standard. BoNT/B or BoNT/E, respectively are diluted in sample buffer and applied to the microtiter plate in a volume of 100 µL/well. Both substances are applied in excess, a dilution of 200 ng/mL is used. Samples and standards are incubated for 2 h at 37° C. Microtiter plates are washed three times with washing buffer. 100 µL of detection buffer/well are added and incubated for 1 h at room temperature. Then microtiter plates are washed three times with washing buffer. Subsequently, the incubation with 100 µL/well of the secondary antibody for 1 h at room temperature is performed. Then microtiter plates are washed three times with washing buffer.

The detection reaction is started by adding 100 µL substrate/well. After incubation for 30 minutes at room temperature the reaction is stopped by adding 50 µL 2 M $H_2SO_4$/well and the absorbance is determined at 450 nm. For determination of specificity the concentrations of BoNT/B and BoNT/E are calculated by standardization. By calculating the recovery rate the specificity of the anti linkerpeptides scBoNT/A for serotypes B and E can be determined. The lower the recovery rate, the lower the cross reactivity and the better the specificity of the serum in regard to scBoNT/A.

b) Specificity of the anti-linkerpeptide scBoNT/A with regard to Dichain BoNT/A: For determination of specificity of the antiserum in regard to activated Dichain-BoNT/A an immunohistological detection by Western blotting is performed. A NT sample (scBoNT/A at least 50 ng, Dichain-BoNT/A dependent on the sample used) is separated under reducing conditions by SDS-PAGE in accordance to their molecular weight into scBoNT/A, LC and HC (Dichain-BoNT/A). The proteins are then blotted onto a PVDF membrane. The membrane is blocked with 20 mL blocking buffer for 1 h at room temperature. The blocking buffer is removed and 20 mL of primary antibody solution containing 0.005 µg/mL anti linkerpeptide scBoNT/A serum are added. The primary antibody is incubated over night at 4° C. The antibody containing solution is removed and the membrane is washed three times for 30 minutes with 20 mL washing buffer at 37° C. Subsequently, the membrane is incubated for 3 h at room temperature with 20 mL of the secondary antibody in a concentration of 0.4 µg/mL. The secondary antibody solution is removed and the membrane is washed three times for 30 minutes with 20 mL washing buffer at 37° C. Additionally, the membrane is washed once with 20 mL of a 25 mM Tris buffer for 5 minutes at room temperature.

The detection reaction is performed by adding the substrate. The substrate is incubated for 15 minutes and the color reaction is stopped by adding water. The specificity is determined by the staining of the scBoNT/A band at 150 kDa. Specificity of the anti linkerpeptide was determined when only the 150 kDa specific band was detected but no band specific for Dichain BoNT/A at 100 kDa (HC) and 50 kDa (LC).

scBoNT/A contents of different charges were determined using the ELISA conditions referred to above and compared to the contents determined by SDS PAGE. The results are shown in the following table.

TABLE scBoNT/A determined by SDS PAGE versus ELISA

| Sample no. | scBoNT/A (%) by SDS PAGE | scBoNT/A (%) by ELISA |
|---|---|---|
| 1 | 9.5 | 11.97 |
| 2 | 0.4 | 0.64 |
| 3 | 0.8 | 0.68 |
| 4 | 3.5 | 3.97 |
| 5 | 0.8 | 0.13 |
| 6 | 2.1 | 1.36 |
| 7 | 1.1 | 1.12 |
| 8 | 1.5 | 1.33 |
| 9 | 2.0 | 1.88 |

The invention claimed is:

1. A method for determining an amount of partially processed and/or unprocessed *Clostridium botulinum* neurotoxin A (BoNT/A) in a solution comprising processed and partially processed and/or unprocessed BoNT/A, wherein the partially processed and unprocessed BoNT/A exhibit a linker peptide, comprising the steps of:
   i) contacting a sample of the solution with a capture antibody which specifically binds to the partially processed and unprocessed BoNT/A under conditions which allow for binding for the antibody to the partially processed and unprocessed BoNT/A, whereby a complex is formed, and
   ii) determining the amount of the complex formed in step i), whereby the amount of the complex is indicative for the amount of the partially processed and/or unprocessed BoNT/A in the solution;
   wherein the capture antibody is obtained by;
   a) contacting a polyclonal antiserum from an animal which has been immunized with a peptide immunogen comprising amino acids 5 to 9 of SEQ ID NO: 1 and/or the amino acid sequence of SEQ ID NO:1 with capture peptides selected from those having an amino acid sequence SLD, LDK and YNK under conditions which allow for the formation of capture complexes comprising unspecific antibodies comprised by the polyclonal antiserum and the capture peptides;
   b) removing the capture complexes from the polyclonal antiserum;
   c) contacting the polyclonal antiserum from step b) with a peptide consisting essentially of SEQ ID NO: E under conditions which allow for the formation of a complex comprising the peptide consisting essentially of SEQ ID NO: 1 and an antibody which specifically binds to unprocessed BoNT/A or partially processed BoNT/A polypeptides which exhibit a linker peptide;
   d) removing the complex formed in step c) from the antiserum; and
   e) releasing the antibody which specifically binds to unprocessed BoNT/A or partially processed BoNT/A polypeptides from the complex.

2. The method of claim 1, wherein the amino acids 5 to 9 of SEQ ID NO: 1 and/or the amino acid sequence of SEQ ID NO:1 of the peptide immunogen is linked to Keyhole Limpet Hemocyanin (KLH).

3. The method of claim 2, wherein the KLH is linked to the amino acids 5 to 9 of SEQ ID NO: 1 and/or the amino acid sequence of SEQ ID NO: 1 via a N-[gamma-maleimidobutyryloxy] succinimide ester (GMBS) linker.

4. The method of claim 1, wherein the conditions which allow for binding of the antibody to the partially processed and unprocessed BoNT/A in step i) comprise the presence of a detergent.

5. The method of claim 4, wherein the detergent is Tween 20.

6. The method of claim 4, wherein the detergent is present at a concentration in the range of from 0.01% (v/v) to 10% (v/v).

7. The method of claim 6, wherein the concentration of the detergent is in the range of from 0.2% (v/v) to 0.8% (v/v) or in the range of from 0.3% (v/v) to 0.6% (v/v).

8. The method of claim 1, wherein the conditions which allow for binding of the antibody to the partially processed and unprocessed BoNT/A in step i) comprise the presence of a phosphate-buffered or tris-buffered saline solution.

9. The method of claim 8, wherein the conditions which allow for binding of the antibody to the partially processed and unprocessed BoNT/A in step i) comprise the presence of NaCl at a concentration in the range of from 150 to 350 mM.

10. The method of claim 9, wherein the concentration of NaCl is in the range of from 200 to 300 mM.

11. The method of claim 1, wherein step ii) comprises comparing the amount of the complex with a reference whereby the amounts of complex determined can be allocated to predefined amounts of unprocessed BoNT/A polypeptide.

* * * * *

UNITED STATES PATENT AND TRADEMARK OFFICE
CERTIFICATE OF CORRECTION

PATENT NO. : 8,841,080 B2  
APPLICATION NO. : 13/503128  
DATED : September 23, 2014  
INVENTOR(S) : Harold Victor Taylor, Karl-Heinz Eisele and Cornelia Brunn Page 1 of 1

It is certified that error appears in the above-identified patent and that said Letters Patent is hereby corrected as shown below:

In the Claims

Column 29, Line 31: "SEQ ID NO: E" should be --SEQ ID NO: 1--.

Signed and Sealed this
Twenty-third Day of December, 2014

Michelle K. Lee
*Deputy Director of the United States Patent and Trademark Office*

SEQUENCE LISTING

<160> NUMBER OF SEQ ID NOS: 9

<210> SEQ ID NO 1
<211> LENGTH: 11
<212> TYPE: PRT
<213> ORGANISM: Clostridium botulinum

<400> SEQUENCE: 1

Thr Lys Ser Leu Asp Lys Gly Tyr Asn Lys Ala
1               5                   10

<210> SEQ ID NO 2
<211> LENGTH: 1296
<212> TYPE: PRT

<213> ORGANISM: Clostridium botulinum

<400> SEQUENCE: 2

```
Met Pro Phe Val Asn Lys Gln Phe Asn Tyr Lys Asp Pro Val Asn Gly
1               5                   10                  15

Val Asp Ile Ala Tyr Ile Lys Ile Pro Asn Ala Gly Gln Met Gln Pro
            20                  25                  30

Val Lys Ala Phe Lys Ile His Asn Lys Ile Trp Val Ile Pro Glu Arg
        35                  40                  45

Asp Thr Phe Thr Asn Pro Glu Glu Gly Asp Leu Asn Pro Pro Pro Glu
    50                  55                  60

Ala Lys Gln Val Pro Val Ser Tyr Tyr Asp Ser Thr Tyr Leu Ser Thr
65                  70                  75                  80

Asp Asn Glu Lys Asp Asn Tyr Leu Lys Gly Val Thr Lys Leu Phe Glu
                85                  90                  95

Arg Ile Tyr Ser Thr Asp Leu Gly Arg Met Leu Leu Thr Ser Ile Val
            100                 105                 110

Arg Gly Ile Pro Phe Trp Gly Gly Ser Thr Ile Asp Thr Glu Leu Lys
        115                 120                 125

Val Ile Asp Thr Asn Cys Ile Asn Val Ile Gln Pro Asp Gly Ser Tyr
    130                 135                 140

Arg Ser Glu Glu Leu Asn Leu Val Ile Gly Pro Ser Ala Asp Ile
145                 150                 155                 160

Ile Gln Phe Glu Cys Lys Ser Phe Gly His Glu Val Leu Asn Leu Thr
                165                 170                 175

Arg Asn Gly Tyr Gly Ser Thr Gln Tyr Ile Arg Phe Ser Pro Asp Phe
            180                 185                 190

Thr Phe Gly Phe Glu Glu Ser Leu Glu Val Asp Thr Asn Pro Leu Leu
        195                 200                 205

Gly Ala Gly Lys Phe Ala Thr Asp Pro Ala Val Thr Leu Ala His Glu
    210                 215                 220

Leu Ile His Ala Gly His Arg Leu Tyr Gly Ile Ala Ile Asn Pro Asn
225                 230                 235                 240

Arg Val Phe Lys Val Asn Thr Asn Ala Tyr Tyr Glu Met Ser Gly Leu
                245                 250                 255

Glu Val Ser Phe Glu Glu Leu Arg Thr Phe Gly Gly His Asp Ala Lys
            260                 265                 270

Phe Ile Asp Ser Leu Gln Glu Asn Glu Phe Arg Leu Tyr Tyr Tyr Asn
        275                 280                 285

Lys Phe Lys Asp Ile Ala Ser Thr Leu Asn Lys Ala Lys Ser Ile Val
    290                 295                 300

Gly Thr Thr Ala Ser Leu Gln Tyr Met Lys Asn Val Phe Lys Glu Lys
305                 310                 315                 320

Tyr Leu Leu Ser Glu Asp Thr Ser Gly Lys Phe Ser Val Asp Lys Leu
                325                 330                 335

Lys Phe Asp Lys Leu Tyr Lys Met Leu Thr Glu Ile Tyr Thr Glu Asp
            340                 345                 350

Asn Phe Val Lys Phe Phe Lys Val Leu Asn Arg Lys Thr Tyr Leu Asn
        355                 360                 365

Phe Asp Lys Ala Val Phe Lys Ile Asn Ile Val Pro Lys Val Asn Tyr
    370                 375                 380

Thr Ile Tyr Asp Gly Phe Asn Leu Arg Asn Thr Asn Leu Ala Ala Asn
385                 390                 395                 400
```

```
Phe Asn Gly Gln Asn Thr Glu Ile Asn Asn Met Asn Phe Thr Lys Leu
                    405                 410                 415

Lys Asn Phe Thr Gly Leu Phe Glu Phe Tyr Lys Leu Leu Cys Val Arg
            420                 425                 430

Gly Ile Ile Thr Ser Lys Thr Lys Ser Leu Asp Lys Gly Tyr Asn Lys
            435                 440                 445

Ala Leu Asn Asp Leu Cys Ile Lys Val Asn Asn Trp Asp Leu Phe Phe
450                 455                 460

Ser Pro Ser Glu Asp Asn Phe Thr Asn Asp Leu Asn Lys Gly Glu Glu
465                 470                 475                 480

Ile Thr Ser Asp Thr Asn Ile Glu Ala Ala Glu Glu Asn Ile Ser Leu
                    485                 490                 495

Asp Leu Ile Gln Gln Tyr Tyr Leu Thr Phe Asn Phe Asp Asn Glu Pro
                500                 505                 510

Glu Asn Ile Ser Ile Glu Asn Leu Ser Ser Asp Ile Ile Gly Gln Leu
            515                 520                 525

Glu Leu Met Pro Asn Ile Glu Arg Phe Pro Asn Gly Lys Lys Tyr Glu
            530                 535                 540

Leu Asp Lys Tyr Thr Met Phe His Tyr Leu Arg Ala Gln Glu Phe Glu
545                 550                 555                 560

His Gly Lys Ser Arg Ile Ala Leu Thr Asn Ser Val Asn Glu Ala Leu
                565                 570                 575

Leu Asn Pro Ser Arg Val Tyr Thr Phe Phe Ser Ser Asp Tyr Val Lys
                580                 585                 590

Lys Val Asn Lys Ala Thr Glu Ala Ala Met Phe Leu Gly Trp Val Glu
            595                 600                 605

Gln Leu Val Tyr Asp Phe Thr Asp Glu Thr Ser Glu Val Ser Thr Thr
            610                 615                 620

Asp Lys Ile Ala Asp Ile Thr Ile Ile Pro Tyr Ile Gly Pro Ala Leu
625                 630                 635                 640

Leu Asn Ile Gly Asn Met Leu Tyr Lys Asp Asp Phe Val Gly Ala Leu
                645                 650                 655

Ile Phe Ser Gly Ala Val Ile Leu Leu Glu Phe Ile Pro Glu Ile Ala
                660                 665                 670

Ile Pro Val Leu Gly Thr Phe Ala Leu Val Ser Tyr Ile Ala Asn Lys
            675                 680                 685

Val Leu Thr Val Gln Thr Ile Asp Asn Ala Leu Ser Lys Arg Asn Glu
            690                 695                 700

Lys Trp Asp Glu Val Tyr Lys Tyr Ile Val Thr Asn Trp Leu Ala Lys
705                 710                 715                 720

Val Asn Thr Gln Ile Asp Leu Ile Arg Lys Lys Met Lys Glu Ala Leu
                725                 730                 735

Glu Asn Gln Ala Glu Ala Thr Lys Ala Ile Ile Asn Tyr Gln Tyr Asn
            740                 745                 750

Gln Tyr Thr Glu Glu Lys Asn Asn Ile Asn Phe Asn Ile Asp Asp
            755                 760                 765

Leu Ser Ser Lys Leu Asn Glu Ser Ile Asn Lys Ala Met Ile Asn Ile
    770                 775                 780

Asn Lys Phe Leu Asn Gln Cys Ser Val Ser Tyr Leu Met Asn Ser Met
785                 790                 795                 800

Ile Pro Tyr Gly Val Lys Arg Leu Glu Asp Phe Asp Ala Ser Leu Lys
                805                 810                 815

Asp Ala Leu Leu Lys Tyr Ile Tyr Asp Asn Arg Gly Thr Leu Ile Gly
```

-continued

```
                820                 825                 830
Gln Val Asp Arg Leu Lys Asp Lys Val Asn Asn Thr Leu Ser Thr Asp
            835                 840                 845
Ile Pro Phe Gln Leu Ser Lys Tyr Val Asp Asn Gln Arg Leu Leu Ser
            850                 855                 860
Thr Phe Thr Glu Tyr Ile Lys Asn Ile Ile Asn Thr Ser Ile Leu Asn
865                 870                 875                 880
Leu Arg Tyr Glu Ser Asn His Leu Ile Asp Leu Ser Arg Tyr Ala Ser
                885                 890                 895
Lys Ile Asn Ile Gly Ser Lys Val Asn Phe Asp Pro Ile Asp Lys Asn
            900                 905                 910
Gln Ile Gln Leu Phe Asn Leu Glu Ser Ser Lys Ile Glu Val Ile Leu
            915                 920                 925
Lys Asn Ala Ile Val Tyr Asn Ser Met Tyr Glu Asn Phe Ser Thr Ser
            930                 935                 940
Phe Trp Ile Arg Ile Pro Lys Tyr Phe Asn Ser Ile Ser Leu Asn Asn
945                 950                 955                 960
Glu Tyr Thr Ile Ile Asn Cys Met Glu Asn Asn Ser Gly Trp Lys Val
                965                 970                 975
Ser Leu Asn Tyr Gly Glu Ile Ile Trp Thr Leu Gln Asp Thr Gln Glu
                980                 985                 990
Ile Lys Gln Arg Val Val Phe Lys Tyr Ser Gln Met Ile Asn Ile Ser
            995                 1000                1005
Asp Tyr Ile Asn Arg Trp Ile Phe Val Thr Ile Thr Asn Asn Arg
            1010                1015                1020
Leu Asn Asn Ser Lys Ile Tyr Ile Asn Gly Arg Leu Ile Asp Gln
            1025                1030                1035
Lys Pro Ile Ser Asn Leu Gly Asn Ile His Ala Ser Asn Asn Ile
            1040                1045                1050
Met Phe Lys Leu Asp Gly Cys Arg Asp Thr His Arg Tyr Ile Trp
            1055                1060                1065
Ile Lys Tyr Phe Asn Leu Phe Asp Lys Glu Leu Asn Glu Lys Glu
            1070                1075                1080
Ile Lys Asp Leu Tyr Asp Asn Gln Ser Asn Ser Gly Ile Leu Lys
            1085                1090                1095
Asp Phe Trp Gly Asp Tyr Leu Gln Tyr Asp Lys Pro Tyr Tyr Met
            1100                1105                1110
Leu Asn Leu Tyr Asp Pro Asn Lys Tyr Val Asp Val Asn Asn Val
            1115                1120                1125
Gly Ile Arg Gly Tyr Met Tyr Leu Lys Gly Pro Arg Gly Ser Val
            1130                1135                1140
Met Thr Thr Asn Ile Tyr Leu Asn Ser Ser Leu Tyr Arg Gly Thr
            1145                1150                1155
Lys Phe Ile Ile Lys Lys Tyr Ala Ser Gly Asn Lys Asp Asn Ile
            1160                1165                1170
Val Arg Asn Asn Asp Arg Val Tyr Ile Asn Val Val Val Lys Asn
            1175                1180                1185
Lys Glu Tyr Arg Leu Ala Thr Asn Ala Ser Gln Ala Gly Val Glu
            1190                1195                1200
Lys Ile Leu Ser Ala Leu Glu Ile Pro Asp Val Gly Asn Leu Ser
            1205                1210                1215
Gln Val Val Val Met Lys Ser Lys Asn Asp Gln Gly Ile Thr Asn
            1220                1225                1230
```

| Lys | Cys | Lys | Met | Asn | Leu | Gln | Asp | Asn | Gly | Asn | Asp | Ile | Gly |
| --- | --- | --- | --- | --- | --- | --- | --- | --- | --- | --- | --- | --- | --- |
| 1235 | | | | 1240 | | | | | 1245 | | | | |

| Phe | Ile | Gly | Phe | His | Gln | Phe | Asn | Asn | Ile | Ala | Lys | Leu | Val | Ala |
| --- | --- | --- | --- | --- | --- | --- | --- | --- | --- | --- | --- | --- | --- | --- |
| 1250 | | | | | 1255 | | | | | 1260 | | | | |

| Ser | Asn | Trp | Tyr | Asn | Arg | Gln | Ile | Glu | Arg | Ser | Ser | Arg | Thr | Leu |
| --- | --- | --- | --- | --- | --- | --- | --- | --- | --- | --- | --- | --- | --- | --- |
| 1265 | | | | | 1270 | | | | | 1275 | | | | |

| Gly | Cys | Ser | Trp | Glu | Phe | Ile | Pro | Val | Asp | Asp | Gly | Trp | Gly | Glu |
| --- | --- | --- | --- | --- | --- | --- | --- | --- | --- | --- | --- | --- | --- | --- |
| 1280 | | | | | 1285 | | | | | 1290 | | | | |

| Arg | Pro | Leu |
| --- | --- | --- |
| 1295 | | |

<210> SEQ ID NO 3
<211> LENGTH: 3891
<212> TYPE: DNA
<213> ORGANISM: Clostridium botulinum

<400> SEQUENCE: 3

```
atgccatttg ttaataaaca atttaattat aaagatcctg taaatggtgt tgatattgct      60
tatataaaaa ttccaaatgc aggacaaatg caaccagtaa aagcttttaa aattcataat     120
aaaatatggg ttattccaga aagagataca tttacaaatc ctgaagaagg agatttaaat     180
ccaccaccag aagcaaaaca agttccagtt tcatattatg attcaacata tttaagtaca     240
gataatgaaa aagataatta tttaaaggga gttacaaaat atttgagag aatttattca      300
actgatcttg aagaatgtt gttaacatca atagtaaggg aataccatt ttggggtgga       360
agtacaatag atacagaatt aaaagttatt gatactaatt gtattaatgt gatacaacca     420
gatggtagtt atagatcaga agaacttaat ctagtaataa taggaccctc agctgatatt     480
atacagtttg aatgtaaaag ctttggacat gaagttttga atcttacgcg aaatggttat     540
ggctctactc aatacattag atttagccca gattttacat ttggttttga ggagtcactt     600
gaagttgata caaatcctct tttaggtgca ggcaaatttg ctacagatcc agcagtaaca     660
ttagcacatg aacttataca tgctggacat agattatatg gaatagcaat taatccaaat     720
agggttttta agtaaatac taatgcctat tatgaaatga gtgggttaga agtaagcttt      780
gaggaactta aacatttggg ggacatgat gcaaagttta gatagttt acaggaaaac        840
gaatttcgtc tatattatta ataagttt aaagatatag caagtacact aataaaagct       900
aaatcaatag taggtactac tgcttcatta cagtatatga aaaatgtttt taaagagaaa     960
tatctcctat ctgaagatac atctggaaaa ttttcggtag ataaattaaa atttgataag    1020
ttatacaaaa tgttaacaga gatttacaca gaggataatt tgttaagtt ttttaaagta     1080
cttaacagaa aaacatattt gaatttgat aaagccgtat ttaagataaa tatagtacct     1140
aaggtaaatt acacaatata tgatggattt aatttaagaa atacaaattt agcagcaaac    1200
tttaatggtc aaaatacaga attaataat atgaattta ctaaactaaa aaattttact     1260
ggattgttg aattttataa gttgctatgt gtaagaggga taataacttc taaaactaaa    1320
tcattagata aggatacaa taggcatta aatgatttat gtatcaaagt taataattgg     1380
gacttgtttt ttagtccttc agaagataat tttactaatg atctaaataa aggagaagaa    1440
attacatctg atactaatat agaagcagca gaagaaaata ttagtttaga tttaatacaa    1500
caatattatt taacctttaa ttttgataat gaacctgaaa atatttcaat agaaatcttt    1560
tcaagtgaca ttataggcca attagaactt atgcctaata tagaaagatt tcctaatgga    1620
aaaaagtatg agttagataa atatactatg ttccattatc ttcgtgctca agaatttgaa    1680
```

```
catggtaaat ctaggattgc tttaacaaat tctgttaacg aagcattatt aaatcctagt    1740
cgtgtttata cattttttc ttcagactat gtaaagaaag ttaataaagc tacggaggca    1800
gctatgtttt taggctgggt agaacaatta gtatatgatt ttaccgatga aactagcgaa    1860
gtaagtacta cggataaaat tgcggatata actataatta ttccatatat aggacctgct    1920
ttaaatatag gtaatatgtt atataaagat gattttgtag gtgctttaat attttcagga    1980
gctgttattc tgttagaatt tataccagag attgcaatac ctgtattagg tacttttgca    2040
cttgtatcat atattgcgaa taaggttcta accgttcaaa caatagataa tgctttaagt    2100
aaaagaaatg aaaaatggga tgaggtctat aaatatatag taacaaattg gttagcaaag    2160
gttaatacac agattgatct aataagaaaa aaaatgaaag aagctttaga aaatcaagca    2220
gaagcaacaa aggctataat aaactatcag tataatcaat atactgagga agagaaaaat    2280
aatattaatt ttaatattga tgatttaagt tcgaaactta atgagtctat aaataaagct    2340
atgattaata taaataaatt tttgaatcaa tgctctgttt catatttaat gaattctatg    2400
atcccttatg gtgttaaacg gttagaagat tttgatgcta gtcttaaaga tgcattatta    2460
aagtatatat atgataatag aggaacttta attggtcaag tagatagatt aaaagataaa    2520
gttaataata cacttagtac agatatacct tttcagcttt ccaaatacgt agataatcaa    2580
agattattat ctacatttac tgaatatatt aagaatatta ttaatacttc tatattgaat    2640
ttaagatatg aaagtaatca tttaatagac ttatctaggt atgcatcaaa aataaatatt    2700
ggtagtaaag taaattttga tccaatagat aaaaatcaaa ttcaattatt taatttagaa    2760
agtagtaaaa ttgaggtaat tttaaaaaat gctattgtat ataatagtat gtatgaaaat    2820
tttagtacta gcttttggat aagaattcct aagtattttta acagtataag tctaaataat    2880
gaatatacaa taataaattg tatggaaaat aattcaggat ggaaagtatc acttaattat    2940
ggtgaaataa tctggacttt acaggatact caggaaataa acaaagagt agttttttaaa    3000
tacagtcaaa tgattaatat atcagattat ataaacagat ggattttgt aactatcact    3060
aataatagat taaataactc taaaatttat ataaatggaa gattaataga tcaaaaacca    3120
atttcaaatt taggtaatat tcatgctagt aataatataa tgtttaaatt agatggttgt    3180
agagatacac atagatatat ttggataaaa tattttaatc tttttgataa ggaattaaat    3240
gaaaagaaa tcaagattt tatgataat caatcaaatt caggtatttt aaaagacttt    3300
tgggtgatt atttacaata tgataaacca tactatatgt taaatttata tgatccaaat    3360
aaatatgtcg atgtaaataa tgtaggtatt agaggttata tgtatcttaa agggcctaga    3420
ggtagcgtaa tgactacaaa cattatttta aattcaagtt tgtataggg gacaaaattt    3480
attataaaaa aatatgcttc tggaaataaa gataatattg ttagaaataa tgatcgtgta    3540
tatattaatg tagtagttaa aaataaagaa tataggttag ctactaatgc atcacaggca    3600
ggcgtagaaa aaatactaag tgcattagaa atacctgatg taggaaatct aagtcaagta    3660
gtagtaatga agtcaaaaaa tgatcaagga ataacaaata aatgcaaaat gaatttacaa    3720
gataataatg ggaatgatat aggctttata ggatttcatc agtttaataa tatagctaaa    3780
ctagtagcaa gtaattggta taatagacaa atagaaagat ctagtaggac tttgggttgc    3840
tcatgggaat ttattcctgt agatgatgga tggggagaaa ggccactgta a             3891
```

<210> SEQ ID NO 4
<211> LENGTH: 7
<212> TYPE: PRT

```
<213> ORGANISM: Artificial Sequence
<220> FEATURE:
<223> OTHER INFORMATION: Tripeptide for affinity purification 1

<400> SEQUENCE: 4

Glu Leu Asp Lys Tyr Asn Cys
1               5

<210> SEQ ID NO 5
<211> LENGTH: 7
<212> TYPE: PRT
<213> ORGANISM: Artificial Sequence
<220> FEATURE:
<223> OTHER INFORMATION: Tripeptide for affinity purification 2

<400> SEQUENCE: 5

Asn Ile Ser Leu Asp Leu Cys
1               5

<210> SEQ ID NO 6
<211> LENGTH: 6
<212> TYPE: PRT
<213> ORGANISM: Artificial Sequence
<220> FEATURE:
<223> OTHER INFORMATION: Tripeptide for affinity purification 3

<400> SEQUENCE: 6

Tyr Tyr Asn Lys Phe Cys
1               5

<210> SEQ ID NO 7
<211> LENGTH: 12
<212> TYPE: PRT
<213> ORGANISM: artificial
<220> FEATURE:
<223> OTHER INFORMATION: linker peptide immunogen

<400> SEQUENCE: 7

Thr Lys Ser Leu Asp Lys Gly Tyr Asn Lys Ala Cys
1               5                   10

<210> SEQ ID NO 8
<211> LENGTH: 11
<212> TYPE: PRT
<213> ORGANISM: artificial
<220> FEATURE:
<223> OTHER INFORMATION: linker peptide immunogen

<400> SEQUENCE: 8

Thr Lys Ser Leu Asp Lys Gly Tyr Asn Lys Cys
1               5                   10

<210> SEQ ID NO 9
<211> LENGTH: 6
<212> TYPE: PRT
<213> ORGANISM: artificial
<220> FEATURE:
<223> OTHER INFORMATION: linker peptide immunogen

<400> SEQUENCE: 9

Asp Lys Gly Tyr Asn Cys
1               5
```